United States Patent [19]

Tanaka et al.

[11] 4,303,590
[45] Dec. 1, 1981

[54] METHOD FOR THE PREPARATION OF A LOWER ALKYL ESTER OF FATTY ACIDS

[75] Inventors: Yoshiro Tanaka, Ichikawa; Akio Okabe; Susumu Ando, both of Chiba, all of Japan

[73] Assignee: Lion Corporation, Tokyo, Japan

[21] Appl. No.: 149,418

[22] Filed: May 13, 1980

[30] Foreign Application Priority Data

May 30, 1979 [JP] Japan ................................. 54-67188

[51] Int. Cl.³ ........................... C11C 3/02; C09F 5/08
[52] U.S. Cl. ........................... 260/410.9 R; 260/428.5
[58] Field of Search ............... 260/410.9 E, 420, 421, 260/428.5

[56] References Cited

U.S. PATENT DOCUMENTS

| | | | |
|---|---|---|---|
| Re. 22,751 | 4/1946 | Trent | 260/410.9 E |
| 1,659,790 | 2/1928 | Starrels | 260/410.9 E |
| 2,383,599 | 8/1945 | Glossop | 260/410.9 E |
| 4,164,506 | 8/1979 | Kawahara | 260/421 |

*Primary Examiner*—John F. Niebling
*Attorney, Agent, or Firm*—Brisebois & Kruger

[57] ABSTRACT

The invention provides a novel method for the preparation of a lower alkyl, e.g. methyl, ester of fatty acid by the alcoholysis reaction of fatty acid glyceride, i.e. naturally occurring oils or fats, with a lower alcohol, according to which high-quality products containing very small amounts of colored or coloring impurities are readily obtained without the necessity of troublesome procedure or expensive apparatus as in the conventional methods. The inventive method is in principle a two-step alcoholysis reaction and the product obtained in the first step is separated from the by-product glycerine and then subjected to the second alcoholysis reaction followed by admixing of an appropriate amount of water and phase separation so that the undesirable impurities transfer into the aqueous layer and readily separated from the ester product.

4 Claims, No Drawings

METHOD FOR THE PREPARATION OF A LOWER ALKYL ESTER OF FATTY ACIDS

BACKGROUND OF THE INVENTION

The present invention relates to a method for the preparation of a lower alkyl ester of fatty acids or, more particularly, to a method for the preparation of a lower alkyl ester of fatty acids of high quality by the process of alcoholysis of a glyceride of fatty acids with a lower alcohol.

A lower alkyl ester of fatty acids such as methyl stearate is a useful industrial intermediate for the manufacture of soaps, higher alcohols, surface active agents and the like and is produced in a large quantity by the process of alcoholysis or transesterification of a glyceride of fatty acids with a lower alcohol such as methyl alcohol, ethyl alcohol and the like.

Since the glyceride of fatty acids used as the starting material in the above process is usually a naturally occurring oil or fat such as tallow or coconut oil, the lower alkyl ester products obtained therefrom unavoidably contain considerable amounts of colored or coloring impurities. Therefore, final products derived from the lower alkyl esters, such as soaps and higher alcohols, also have problems in the appearance and purity caused by the colored or coloring impurities contained in the intermediate material unless the intermediate material is used with further purification.

The impurities contained in the lower alkyl esters of fatty acids are known to belong to aldehyde compounds or phospholipid compounds of certain kinds and various attempts have been made to remove these impurity compounds from the product (see, for example, Japanese Pat. No. 53-114806).

The colored impurities contained in the lower alkyl esters of fatty acids are removed, in the prior art, by the method of rectification distillation, adsorption with activated clay or other adsorbents or treatment with an alkali. The former two methods are disadvantageous because the procedures are very complicated and troublesome in addition to the increased production costs by the reason of low yield of the desired products. The third method of alkali treatment utilizes a principle that, when a small amount of alkali such as sodium hydroxide is added as an aqueous solution into the reaction mixture of the alcoholysis reaction, the colored or coloring impurities are taken into the solution of the sodium salt of the fatty acids produced by the reaction of sodium hydroxide with the glyceride and separated from the product. This method also suffers from low economy due to low yields of the product.

SUMMARY OF THE INVENTION

It is therefore an object of the present invention to provide a novel and improved method for the preparation of a lower alkyl ester of fatty acids of high quality free from any colored or coloring impurities by the alcoholysis reaction of a naturally occurring fat or oil with a lower alcohol.

Another object of the present invention is to provide an economical way of preparing a lower alkyl ester of fatty acids of high quality from a naturally occurring fat or oil by a very simple and convenient procedure other than the conventional troublesome and expensive procedures such as rectification, adsorption and alkali treatment.

The inventive method, established as a result of extensive investigations by the inventors with the above objects, utilizes a principle that, when a crude product of alcoholysis reaction after removal of glycerine is subjected to a further alcoholysis reaction followed by admixing of a small amount of water and phase separation, the colored impurities are transferred effectively to the aqueous layer and separated from the product.

Thus, the method of the present invention for the preparation of a lower alkyl ester of fatty acids of high quality comprises the steps of (a) esterifying a fatty acid glyceride by the first alcoholysis reaction with a lower alcohol in the presence of an alkali catalyst to form a first crude esterification product and glycerine, (b) separating the glycerine from the first crude esterification product, (c) esterifying further the first crude esterification product by the second alcoholysis reaction with the lower alcohol in the presence of an alkali catalyst to form a second crude esterification product containing the unreacted lower alcohol and glycerine as dissolved or dispersed therein, (d) admixing the second crude esterification product with water in an amount from 50% to 150% by weight based on the amount of the lower alcohol contained in the second crude esterification product, and (e) subjecting the second crude esterification product admixed with water to phase separation into the aqueous layer and the layer of the lower alkyl ester of fatty acids.

DETAILED DESCRIPTION OF THE PREFERRED EMBODIMENTS

The first alcoholysis reaction as the step (a) in the inventive method is conventional and need not be described in detail.

The fatty acid glyceride as the starting material of the inventive method may be any kind of naturally occurring vegetable-origin or animal-origin fats or oils including palm oil, palm kernel oil, cottonseed oil, coconut oil and soybean oil as the examples of the former class and beef tallow, hog fat and various kinds of fish oils as the examples of the latter class. The main ingredients of these fats or oils are glycerides of several kinds of fatty acids containing considerable amounts of impurities such as aldehyde compounds, phospholipid compounds and free fatty acids. They are used without any purification but may be subjected to partial purification prior to the alcoholysis reaction, if desired. In particular, it is sometimes recommendable that the free fatty acids mentioned above as a class of impurities are esterified in advance by a preliminary reaction with the lower alcohol to decrease the acid value of the glyceride so that the fatty acid glyceride used as the starting material of the inventive method contains small amounts of the lower alkyl esters which may be the identical compounds with the objective products.

The lower alcohol used in the first alcoholysis reaction of the fatty acid glyceride is an aliphatic alcohol having from 1 to 3 carbon atoms in a molecule exemplified by methyl alcohol, ethyl alcohol, 1-propyl alcohol and 2-propyl alcohol although the principle of the inventive method is not limited to these alcohols. Among the above named alcohols, methyl alcohol is the most widely used because of the largest demand for the methyl esters.

The alkali catalyst used in the first alcoholysis reaction is also conventional including hydroxides and methylates of sodium and potassium.

The procedure of the first alcoholysis reaction in step (a) is carried out according to a known method, in which the fatty acid glyceride is admixed with a lower alcohol in an amount of 2 to 10 equivalents and an alkali catalyst in an amount of 0.1 to 1.0% by weight based on the fatty acid glyceride and the reaction mixture is heated at or near the boiling temperature of the lower alcohol for about 0.5 to 2 hours under agitation until the reaction has come to substantial termination by establishment of equilibrium. A conversion of 90 to 97% is usually obtained to form a blend of the first crude esterification product and glycerine.

The next step is the separation of the above obtained first crude esterification product and the glycerine. This phase separation can be effected readily by merely standing the reaction mixure for 1 to 15 minutes at 40° to 70° C. so that no particular means for accelerating phase separation, such as centrifugal separation, is usually required.

The crude esterification product obtained in step (a) above and separated in step (b) from the glycerine is then subjected to the second alcoholysis reaction in step (c). The lower alcohol used in the second alcoholysis reaction is usually the same one as in the first alcoholysis reaction and the reaction temperature is also in the same range. Thus, 100 parts by weight of the first crude esterification product is admixed with from 5 to 50 parts by weight or, preferably, from 8 to 20 parts by weight of the lower alcohol and from 0.2 to 0.5 parts by weight of the alkali catalyst and the reaction is carried out under agitation for about 5 to 60 minutes. An overall conversion of 98% or more of the starting fatty acid glyceride is readily obtained to give the second crude esterification product blended with a small amount of glycerine as well as the unreacted alcohol. This blend of the second crude esterification product and the glycerine forms a stable dispersion and cannot be separated into the phases of the former and the latter even by prolonged standing as such.

The above obtained second crude esterification product containing the unreacted lower alcohol, impurities and glycerine is then admixed with water in an amount of 50 to 150% by weight or, preferably, 50 to 100% by weight based on the amount of the unreacted lower alcohol contained therein and stirred uniformly. The addition of water in a limited amount as above is very essential in the inventive method since smaller amounts of water than 50% by weight bring about difficulties and prolongation of time in the subsequent phase separation while larger amounts of water than 150% by weight produce a very stable emulsion hardly separated into phases.

The reaction mixture thus admixed with water is then kept standing at a temperature of 40° to 70° C. whereby phase separation takes place. Though dependent on the height of the liquid layer, the phase separation is complete usually within 15 minutes but it is optional to use a means to accelerate the phase separation such as centrifugal separation, if desired. The lower limit 40° C. of the temperature is recommended since the velocity of phase separation is decreased at below 40° C. due to the partial solidification of certain ingredients in the reaction mixture. The lower layer formed by the phase separation is the aqueous mixture containing the unreacted lower alcohol, glycerine and colored impurities while the upper layer is composed of the objective lower alkyl ester of fatty acids with high quality which is readily separated from the lower layer.

It should be noted that admixing of water to the first crude esterification product after separation of the glycerine is very detrimental to the purpose of impurity removal since emulsification of the reaction mixture takes place by the addition of water and the phase separation of the resultant emulsion is carried out with great difficulties with accumulation of large amounts of sludge-like substances in the interfacial layer of the upper and the lower layers leading to a considerable loss in the yield of the objective product.

As is understood from the description above, high quality products of lower alkyl esters of fatty acids are readily obtained by the method of the present invention and the products with almost no coloration and high purity can be used for manufacturing soaps, higher alcohols and the like excellent in quality also without coloration.

Furthermore, the method of the present invention is very advantageous economically because the two-step alcoholysis reaction of the inventive method gives a higher yield of the product with a conversion of at least 98% or, usually, 99.5% than in the conventional method in addition to the advantages obtained by the simple equipment with only several additional vessels for the reaction and phase separation in comparison with the conventional processes such as rectification, adsorption and alkali treatment using expensive apparatuses.

Following are the examples to illustrate the inventive method in further detail. In the examples, the degree of coloration of the lower alkyl ester products was evaluated as such or for the saponified pastes and the salted-out pastes obtained with the ester products by the procedures described below. The degree of coloration was determined by comparing the sample or a solution of the sample with a series of diluted APHA solutions prepared as below.

Determination of coloration with saponified paste: 10 g of the ester sample was dissolved in 80 g of ethyl alcohol with admixture of sodium hydroxide as a 30% aqueous solution in an amount of 1.03 equivalents of the stoichiometric amount required for complete saponification and the solution was heated for 1 hour at 80° to 90° C. on a warm bath to effect saponification of the ester.

After the free alkali content was adjusted to 0.01% based on the dry soap content by adding a free fatty acid such as stearic acid, ethyl alcohol and water were removed from the reaction mixture and the thus dehydrated saponified paste was re-dissolved in water to give an aqueous solution of 15.7% concentration, which was compared with the APHA solutions to evaluate the degree of coloration.

Determination of coloration with salted-out paste: the above obtained saponified paste containing 37.5% by weight of water was admixed with solid sodium chloride so as that the total amount of electrolytes was in the range from 1.38 to 1.48% and agitated for 15 minutes at a temperature of 90° C. or higher followed immediately by centrifugal separation at 90° to 100° C. for 10 minutes in a centrifugal separator rotating at 2000 r.p.m.

The soap constituent in the upper layer was taken out as the salted-out paste which was dissolved in water to give an aqueous solution of 15.7% concentration as soap to be compared with the APHA solutions for evaluating the degree of coloration.

Determination of the degree of coloration with APHA solutions: a master APHA solution, which was designated as APHA #500 solution, was prepared by dissolving potassium chloroplatinate $K_2PtCl_6$ in an amount of 0.500 g as platinum and cobalt chloride $CoCl_2$ in an amount of 0.250 g as cobalt in 100 ml of hydrochloric acid followed by dilution to 1000 ml with water. The master solution was successively diluted with water to give a series of diluted APHA solutions which were each given an APHA number equal to the number of milligrams of platinum in 1000 ml of the solution. For example, a diluted APHA solution containing 10 mg/1000 ml of platinum obtained by 50 times dilution of the master solution with water was given a number of APHA #10. The degree of coloration of samples was determined by comparing the sample visually with several of the APHA solutions having about the same degree of coloration and recorded by the number of the APHA solution having the closest degree of coloration to the sample.

EXAMPLE 1

(Experiments No. 1 to No. 6)

The starting material of the fatty acid glyceride was a beef tallow of an acid value of 2.0 or below containing 0.5% by weight of fatty acid methyl esters produced by the preliminary esterification of the free fatty acids in the raw tallow with methyl alcohol in a conventional procedure. Into an autoclave of 1000 ml capacity equipped with a stirrer were introduced 500 g of the above beef tallow, 200 g of methyl alcohol and 1.7 g of sodium hydroxide and the mixture was heated at 60° to 70° C. for about 1 hour under agitation to effect the alcoholysis reaction. The conversion of the glyceride into the ester was 96.5%. With the agitation stopped, the reaction mixture was kept standing to be separated into two layers composed of the upper layer of the crude esterification product and the lower layer of glycerine diluted with unreacted methyl alcohol. The volume ratio of the upper and the lower layers was about 4:1.

The upper layer separated from the lower layer was further admixed with 50 g of methyl alcohol and 1.0 g of sodium hydroxide and the second esterification reaction was carried out at 60° to 70° C. for 30 minutes with agitation. The overall conversion of the starting glyceride was 99.1% and the resultant reaction mixture containing about 20% by weight of methyl alcohol was cloudy in appearance.

In the next place, water was added to the reaction mixture in an amount indicated in Table 1 below up to 5 times by weight of the amount of methyl alcohol remaining in the reaction mixture as unreacted and the reaction mixture was agitated for 10 minutes. When the reaction mixture thus admixed with water was kept standing for several minutes at 40° C. or above, phase separation into two layers took place provided that the weight ratio of the added water to the methyl alcohol was within a range. The upper layer was the desired ester product of high quality and the lower layer was composed of water, methyl alcohol and glycerine. The ester product in the upper layer separated from the lower layer was analyzed for the contents of glycerine, methyl alcohol and water contained therein as impurities to give the results set out in Table 1 together with the degree of coloration of the ester layer. Meanwhile, no phase separation took place in the reaction mixture after completion of the second esterification reaction when kept for 2 hours or longer without the addition of water. This reaction mixture contained 0.9% of glycerine and 16.0% of methyl alcohol while the content of the ester product was 82.9% and the degree of coloration was 390 in the APHA scale.

TABLE 1

| Experiment No. | | 1 | 2 | 3 | 4 | 5 | 6 |
|---|---|---|---|---|---|---|---|
| Water/methyl alcohol weight ratio | | 0.2 | 0.5 | 1.0 | 1.5 | 2.0 | 5.0 |
| Time for complete phase separation, minutes | | 20 | 3 | 4 | 4.5 | (*) | (*) |
| Composition of ester layer, % | glycerine | 0.50 | 0.04 | 0.02 | 0.01 | — | — |
| | methyl alcohol | 10.0 | 1.89 | 1.16 | 0.72 | — | — |
| | water | 1.0 | 0.61 | 0.49 | 0.48 | — | — |
| | ester | 88.50 | 97.46 | 98.33 | 98.79 | — | — |
| Coloration of ester layer, APHA | | 340 | 270 | 270 | 270 | — | — |

(*) Stable emulsion was formed in which no phase separation took place even by standing for 2 hours or longer.

EXAMPLE 2

(Experiments No. 7 and No. 9)

The experimental procedure in Experiment No. 7 was the same to the second esterification reaction as in Example 1 and the reaction mixture was admixed with 50 g of water corresponding to about 50% by weight of the unreacted methyl alcohol in the reaction mixture followed by phase separation in the same manner as in Example 1.

The above obtained ester product as well as the saponified paste and the salted-out paste derived therefrom were examined for the degree of coloration in accordance with the testing methods described before. The results are set out in Table 2 below.

For comparison (Experiment No. 8), the first esterification reaction was carried out in just the same manner as in Example 1 to give a first crude esterification product with 96.5% conversion of the starting glyceride.

The above obtained crude esterification product was directly admixed with 50 g of water and agitated for 10 minutes followed by heating to remove methyl alcohol and part of water up to a temperature of 120° C. taking about 2 hours where heating was stopped. When the reaction mixture was kept standing at about 60° C. for 3 hours, phase separation took place into an upper layer of the ester product and a lower layer of glycerine in a volume ratio of about 9:1. The conversion of the starting glyceride at this stage was found to have decreased to 95.5%. The degree of coloration was examined for this ester product as well as for the saponified paste and the salted-out paste derived therefrom to give the results set out in Table 2.

For further comparison (Experiment No. 9), the same experimental procedure as in Example 1 was undertaken to the second esterification reaction to give a second esterification product with 99.1% conversion of the starting glyceride. This reaction mixture was heated up to a temperature of 120° C. for removing the unreacted methyl alcohol as in Experiment No. 8 above followed by standing at 60° C. for 3 hours. The conversion of the starting glyceride was 97.5% at this stage.

The degree of coloration was examined for this ester product as well as the saponified paste and the salted-out paste derived therefrom to give the results set out in Table 2.

As is clear from the results shown in Table 2, the lower alkyl ester of fatty acids obtained according to the inventive method has remarkably low degree of coloration not only as the ester per se but also as a saponified paste or as a salted-out paste.

TABLE 2

| Experiment No. | Coloration of ester, APHA | Coloration of saponified paste, APHA | Coloration of salted-out paste, APHA |
|---|---|---|---|
| 7 | 270 | 150 | 50 |
| 8 | 360 | 190 | 100 |
| 9 | 270 | 170 | 70 |

What is claimed is:

1. A method for the preparation of a lower alkyl ester of fatty acids by the alcoholysis reaction of a fatty acid glyceride with a lower alcohol which comprises the successive steps of
   (a) esterifying the fatty acid glyceride by a first alcoholysis reaction with a lower alcohol in the presence of an alkali catalyst to form a first crude esterification product and glycerine, the conversion of the fatty acid glyceride being in the range of 90–97%,
   (b) separating the glycerine from the first crude esterification product,
   (c) esterifying further said crude esterification product in a second alcoholysis reaction with a lower alcohol in the presence of an alkali catalyst at an overall conversion of at least 98% to form a second crude esterification product containing the unreacted lower alcohol and glycerine dissolved or dispersed therein,
   (d) admixing the second crude esterification product with water in an amount from 50% to 150% by weight based on the amount of the lower alcohol contained in the second crude esterification product, and
   (e) subjecting the second crude esterification product admixed with water to phase separation into an aqueous layer and a layer of the lower alkyl ester of fatty acids.

2. The method as set forth in claim 1 wherein the amount of water added to the second crude esterification product in step (d) is in the range from 50% to 100% by weight based on the amount of the lower alcohol contained in the second crude esterification product.

3. The method as set forth in claim 1 wherein the second alcoholysis reaction set forth in step (c) is carried out by admixing 100 parts by weight of the first crude esterification product with from 5 to 50 parts by weight of the lower alcohol and from 0.2 to 0.5 part by weight of the alkali catalyst.

4. The method as set forth in claim 1 wherein the phase separation of the second crude esterification product in step (e) is carried out at a temperature in the range of from 40 to 70° C.

* * * * *